(12) United States Patent
Bettuchi et al.

(10) Patent No.: US 8,012,129 B2
(45) Date of Patent: Sep. 6, 2011

(54) SURGICAL PORTAL APPARATUS WITH WAFFLE SEAL

(75) Inventors: Michael Bettuchi, Middletown, CT (US); Richard D. Gresham, Guilford, CT (US)

(73) Assignee: Tyco Healthcare Group LP, New Haven, CT (US)

( * ) Notice: Subject to any disclaimer, the term of this patent is extended or adjusted under 35 U.S.C. 154(b) by 0 days.

(21) Appl. No.: 12/468,133

(22) Filed: May 19, 2009

(65) Prior Publication Data

US 2009/0326467 A1 Dec. 31, 2009

Related U.S. Application Data

(60) Provisional application No. 61/075,533, filed on Jun. 25, 2008.

(51) Int. Cl.
*A61M 5/178* (2006.01)
(52) U.S. Cl. .......... 604/167.06; 604/167.01; 604/164.01
(58) Field of Classification Search .............. 604/165.01–167.06, 108
See application file for complete search history.

(56) References Cited

U.S. PATENT DOCUMENTS

| | | |
|---|---|---|
| 2,602,028 A | 7/1952 | Urban et al. |
| 4,769,018 A | 9/1988 | Wilson |
| 5,104,383 A | 4/1992 | Shichman |
| 5,127,909 A | 7/1992 | Shichman |
| 5,209,737 A | 5/1993 | Ritchart et al. |
| 5,267,966 A | 12/1993 | Paul |
| 5,273,533 A | 12/1993 | Bonaldo |
| 5,290,245 A | 3/1994 | Dennis |
| 5,304,143 A | 4/1994 | Green et al. |
| 5,308,336 A | 5/1994 | Hart et al. |
| 5,342,315 A | 8/1994 | Rowe et al. |
| 5,385,553 A | 1/1995 | Hart et al. |
| 5,391,154 A | 2/1995 | Young |
| 5,549,565 A | 8/1996 | Ryan et al. |
| 5,554,124 A | 9/1996 | Alvarado |
| 5,569,206 A | 10/1996 | Gorman, Jr. et al. |
| 5,584,850 A | 12/1996 | Hart et al. |
| 5,603,702 A | 2/1997 | Smith et al. |

(Continued)

FOREIGN PATENT DOCUMENTS

EP 1679043 7/2006

OTHER PUBLICATIONS

European Search Report, Application No. EP 09 25 1621, dated Dec. 7, 2009.

(Continued)

*Primary Examiner* — Nicholas D Lucchesi
*Assistant Examiner* — Leah Stohr

(57) ABSTRACT

A surgical portal apparatus includes a portal housing, an elongated portal member connected to the portal housing and depending therefrom, and a seal member comprising a resilient material and being mounted to the portal housing. The portal housing and the portal member have an axial bore for reception and passage of a surgical object. The seal member includes leading and trailing faces and has inner portions defining a passage to permit passage of a surgical object. One of the leading and trailing faces defines a plurality of recessed cells formed within interconnected struts. The interconnected struts are relatively flexible to flex upon radial offset manipulation of the object to permit corresponding movement of the passage while substantially maintaining a seal about the surgical object. At least some of the recessed cells define a generally rectangular arrangement. Preferably, the leading end face of the seal member has the recessed cells.

16 Claims, 5 Drawing Sheets

U.S. PATENT DOCUMENTS

| | | | |
|---|---|---|---|
| 5,685,854 A | 11/1997 | Green et al. | |
| 5,709,664 A * | 1/1998 | Vandenbroek et al. | 604/167.04 |
| 5,755,702 A | 5/1998 | Hillstead et al. | |
| 5,858,008 A | 1/1999 | Capaccio | |
| 5,925,013 A | 7/1999 | Exline et al. | |
| 6,024,755 A | 2/2000 | Addis | |
| RE36,702 E | 5/2000 | Green et al. | |
| 6,551,282 B1 | 4/2003 | Exline et al. | |
| 6,595,946 B1 | 7/2003 | Pasqualucci | |
| 6,663,599 B2 | 12/2003 | Osbourne et al. | |
| 6,702,787 B2 | 3/2004 | Racenet et al. | |
| D499,484 S | 12/2004 | Blanco | |
| 6,942,671 B1 | 9/2005 | Smith | |
| 6,981,966 B2 | 1/2006 | Green et al. | |
| 7,025,747 B2 | 4/2006 | Smith | |
| 7,165,568 B2 | 1/2007 | Kessell et al. | |
| 7,390,317 B2 | 6/2008 | Taylor et al. | |
| 7,470,255 B2 | 12/2008 | Stearns et al. | |
| 7,559,918 B2 | 7/2009 | Pasqualucci | |
| 7,563,250 B2 | 7/2009 | Wenchell | |
| 7,582,071 B2 | 9/2009 | Wenchell | |
| 7,585,288 B2 | 9/2009 | Haberland et al. | |
| 7,608,082 B2 | 10/2009 | Cuevas et al. | |
| 7,632,250 B2 | 12/2009 | Smith et al. | |
| 2004/0082909 A1 | 4/2004 | Shia et al. | |
| 2004/0106942 A1 | 6/2004 | Taylor et al. | |
| 2004/0140285 A1 | 7/2004 | Vetter et al. | |
| 2004/0167559 A1 | 8/2004 | Taylor et al. | |
| 2004/0215209 A1 | 10/2004 | Almond et al. | |
| 2005/0085774 A1 | 4/2005 | Streifinger et al. | |
| 2005/0096695 A1 | 5/2005 | Olich | |
| 2005/0203467 A1 * | 9/2005 | O'Heeron et al. | 604/249 |
| 2005/0261661 A1 * | 11/2005 | McFarlane | 604/506 |
| 2005/0288634 A1 | 12/2005 | O'Heeron et al. | |
| 2006/0020281 A1 | 1/2006 | Smith | |
| 2006/0047284 A1 | 3/2006 | Gresham | |
| 2006/0253077 A1 | 11/2006 | Smith | |
| 2007/0093851 A1 | 4/2007 | Moran et al. | |
| 2007/0179403 A1 | 8/2007 | Heske et al. | |
| 2007/0260186 A1 | 11/2007 | Lang | |
| 2008/0077169 A1 | 3/2008 | Taylor et al. | |
| 2008/0091144 A1 | 4/2008 | Moran et al. | |
| 2008/0275406 A1 | 11/2008 | Smith | |
| 2008/0287877 A1 | 11/2008 | Gresham et al. | |
| 2008/0294113 A1 * | 11/2008 | Brockmeier et al. | 604/167.06 |
| 2009/0005740 A1 | 1/2009 | Smith | |
| 2009/0076465 A1 | 3/2009 | Berry et al. | |
| 2009/0082720 A1 | 3/2009 | Smith | |
| 2009/0105635 A1 | 4/2009 | Bettuchi et al. | |
| 2009/0209915 A1 | 8/2009 | Zastawny et al. | |
| 2009/0259185 A1 | 10/2009 | Okoniewski | |
| 2009/0292251 A1 | 11/2009 | Wenchell | |
| 2009/0318868 A1 | 12/2009 | Racenet et al. | |

OTHER PUBLICATIONS

US 7,282,043, 10/2007, Racenet et al. (withdrawn)

* cited by examiner

SURGICAL PORTAL APPARATUS WITH WAFFLE SEAL

CROSS REFERENCE TO RELATED APPLICATION

The present application claims the benefit of and priority to U.S. Provisional Application Ser. No. 61/075,533 filed on Jun. 25, 2008, the entire contents of which are incorporated herein by reference.

BACKGROUND

1. Technical Field

The present disclosure relates to a surgical portal for accessing underlying body tissue to permit the introduction of surgical objects in conjunction with a medical procedure. More particularly, the present disclosure relates to a surgical portal including a seal defining a gridiron or waffle pattern adapted to flex and facilitate offset manipulation of a surgical object while substantially maintaining a sealing relation therewith.

2. Discussion of Related Art

Surgical portals are employed in various minimally invasive procedures including laparoscopic or endoscopic procedures. Such portals are inclusive of trocar cannulas, catheters, or, in the event of a minimally invasive hand assist procedures, hand access devices. Surgical portals typically incorporate a seal mechanism to form a fluid tight seal about an instrument or hand passed through the portal. The seal mechanisms, however, often are limited by their ability to sustain a seal when an instrument, particularly, a smaller diameter instrument, is moved off-axis relative to a central axis of the portal. Moreover, the seal mechanisms are also limited by their ability to sustain their integrity when the surgical instrument is angulated. Such extreme ranges of motion of smaller diameter surgical instruments within the portal can create a "cat eye" or crescent shaped gap about the instrument resulting in fluid loss (e.g., insufflation gas loss).

SUMMARY

Accordingly, the present disclosure is directed to a surgical portal apparatus. The surgical portal apparatus includes a portal housing, an elongated portal member connected to the portal housing and depending therefrom, and a seal member comprising a resilient material and being mounted to the portal housing. The portal housing and the portal member have an axial bore for reception and passage of a surgical object. The seal member includes leading and trailing faces and has inner portions defining a passage to permit passage of a surgical object. One of the leading and trailing faces defines a plurality of recessed cells formed within interconnected struts. The interconnected struts are relatively flexible to flex upon radial offset manipulation of the object to permit corresponding movement of the passage while substantially maintaining a seal about the surgical object. At least some of the recessed cells define a generally rectangular arrangement. Preferably, the leading end face of the seal member has the recessed cells.

The trailing end face of the seal member may define a seal recess circumscribing the passage to facilitate reception and passage of the surgical object through the passage. The seal recess may be generally annular. The seal member may include an annular seal collar depending from the trailing end face. The annular seal collar includes an internal wall surface which may be tapered to facilitate alignment of the surgical object with the passage during introduction of the surgical object within the seal member. The trailing end face may include an internal tapered wall circumscribing the passage to facilitate alignment of the surgical object with the passage during passage through the seal member.

The seal member may define an aperture therethrough functioning as the passage. The seal member may comprise a gel material. A zero closure seal may be disposed within the portal housing to substantially close the axial bore in the absence of the surgical object.

Other embodiments are also envisioned.

BRIEF DESCRIPTION OF THE DRAWINGS

Preferred embodiments of the present disclosure will be better appreciated by reference to the drawings wherein.

DETAILED DESCRIPTION OF THE EMBODIMENTS

The portal apparatus of the present disclosure is capable of accommodating objects of varying diameters, e.g., including instruments from about 4.5 millimeter (mm) to about 15 millimeter (mm), during a minimally invasive surgical procedure. Moreover, the portal apparatus contemplates the introduction and manipulation of various types of surgical objects or instrumentation adapted for insertion through a trocar and/or cannula assembly while maintaining a fluid tight interface about the instrumentation to prevent gas and/or fluid leakage from the established pneumoperitoneum so as to preserve the atmospheric integrity of a surgical procedure. Specifically, the portal apparatus includes a seal assembly which facilitates lateral and/or angular manipulation of the surgical instrument while also maintaining a seal about the instrument.

Examples of instrumentation contemplated for use with the portal apparatus include clip appliers, graspers, dissectors, retractors, staplers, laser probes, photographic devices, endoscopes and laparoscopes, tubes, obturators and the like. Such instruments will be collectively referred to herein as "instruments or instrumentation".

In the following discussion, the term "proximal" or "trailing" will refer to the portion of the portal apparatus nearest to the clinician during operation while the term "distal" or "leading" will refer to that portion of the portal apparatus most remote to the clinician.

Figure 1:
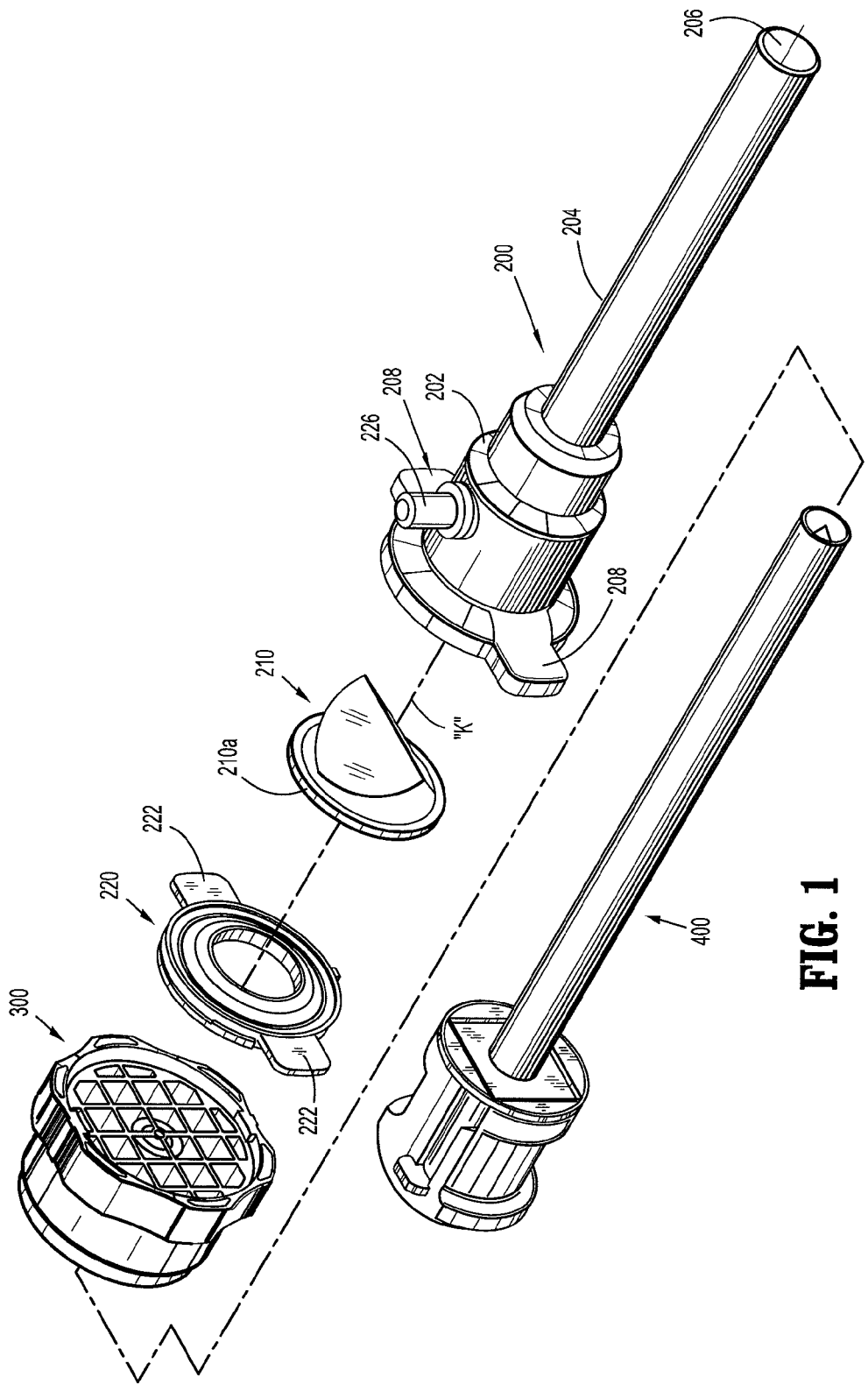
FIG. 1 is a perspective view with parts separated of the surgical portal apparatus in accordance with the principles of the present disclosure illustrating, the seal assembly and the surgical portal assembly.

Referring now to the drawings, in which like reference numerals identify identical or substantially similar parts throughout the several views, FIG. 1 illustrates the portal apparatus 100 of the present disclosure. Portal apparatus 100 includes portal assembly 200 and seal assembly 300. Seal assembly 300 may be an integral component of portal assembly 200, or, in the alternative, may be releasably connectable to the portal assembly 200 via various contemplated means. Seal assembly 300 will be discussed in greater detail hereinbelow. Portal assembly 200 may be any member suitable for the intended purpose of accessing a body cavity and typically defines a passageway permitting introduction of instruments or the clinician's hand therethrough. Portal assembly 200 is particularly adapted for use in laparoscopic surgery where the peritoneal cavity is insufflated with a suitable gas, e.g., $CO_2$, to raise the cavity wall from the internal organs therein. Portal assembly 200 is typically used with an obturator assembly 400 which may be blunt, a non-bladed, or a sharp pointed instrument positionable within the passageway of the portal apparatus 100. Obturator assembly 400 is utilized to penetrate the abdominal wall to introduce the portal apparatus 100 through the abdominal wall, and then subsequently is removed from the portal assembly 200 to permit introduction of the surgical instrumentation utilized to perform the procedure through the passageway. An example of suitable obturator assembly 400 is disclosed in commonly assigned U.S. Pat. No. 6,497,716 to Green et al., the entire contents of which are incorporated herein by its entirety.

Portal assembly 200 includes portal housing 202 and portal member 204 connected to the portal housing 202 and extending therefrom. Portal member 204 defines a longitudinal axis "k" extending along the length of the portal member 204. Portal housing 202 and portal member 204 further define internal longitudinal passage 206 dimensioned to permit passage of surgical instrumentation. Portal member 204 may be formed of any suitable medical grade material, such as stainless steel or other rigid materials, including polymeric materials, such as polycarbonate, or the like. Portal member 204 may be transparent or opaque. The diameter of portal member 204 may vary, but, typically ranges from about 4.5 millimeters (mm) to about 15 millimeters (mm). Portal housing 202 and portal member 204 may be separate components securely connected to each other, or, in the alternative may be a single monolithically formed unit.

Figure 2:
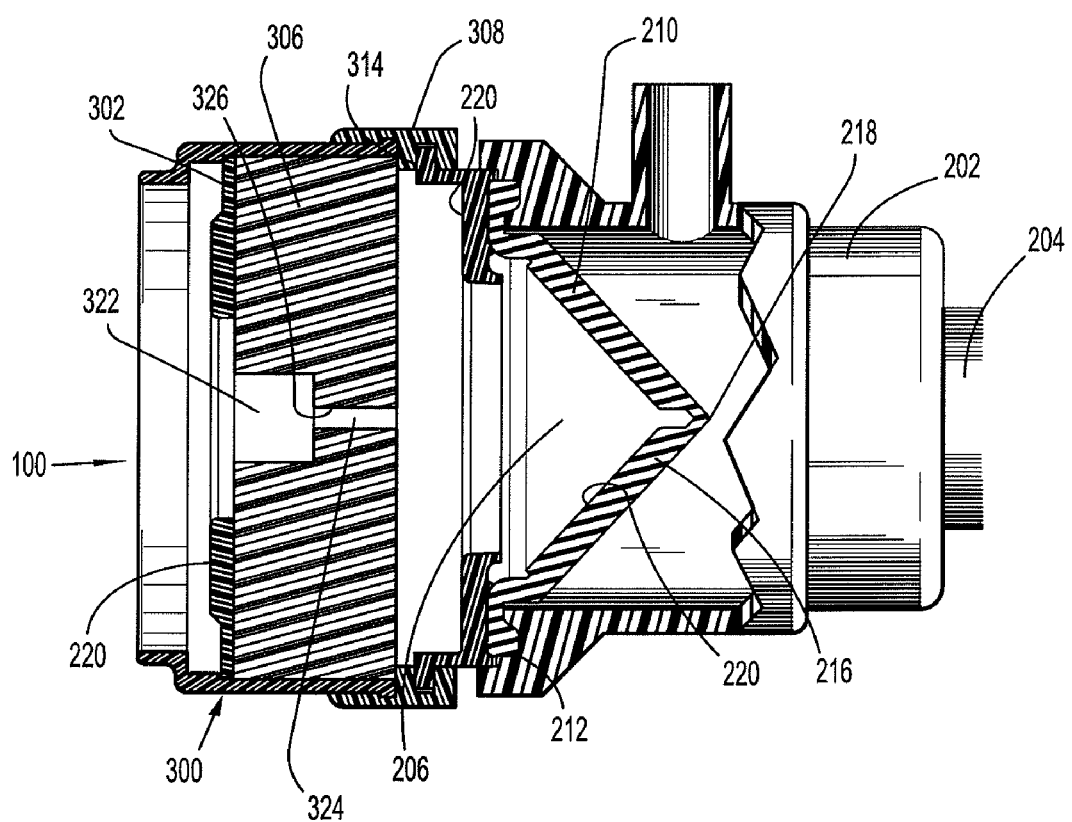
FIG. 2 is a side cross-sectional view of the seal assembly and the portal housing of the surgical portal assembly.

Referring now to FIGS. 1-2, portal housing 202 defines a generally circular cross-section and possesses diametrically opposed leg portions 208. Zero closure seal 210 fabricated from a resilient material, e.g., rubber, is positioned within the interior of portal housing 202. Seal 210 includes circumferential flange portion 210a which rests on a correspondingly dimensioned circumferential ledge 212 within portal housing 202. Seal 210 generally defines a duck bill shape having two planar tapering portions 216 which intersect at their distal ends to define slit 218. Slit 218 permits passage of the elongated object through the seal 210, but, in the absence of an instrument, and particularly when portal member 204 is positioned within an insufflated body cavity, slit 218 closes to seal longitudinal passage 206. Seal 210 also includes at least one, preferably two, reinforcing ribs 220 to stabilize the seal. Ribs 220 are positioned to engage the instrument to guide the instrument through slit 218 and prevent piercing of the seal 210 by the tip of the instrument.

Portal assembly 200 also includes stabilizing plate 220 which is positioned against flange portion 210a of seal 208 to provide support for seal 208 during introduction and withdrawal of an elongated instrument. Stabilizing plate 220 includes two diametrically opposed extensions 222 (FIG. 1) which are received within the correspondingly dimensioned leg portions 228 of portal housing 202. In the preferred embodiment, stabilizing plate 220 is securely attached to the portal housing 202 at contact points along the extensions of the respective components by spot welding, adhesives or the like.

Stop cock valve 226 may be incorporated as part of portal housing 202 to permit the passage of insufflation gases through portal member 204 and into the body cavity. A suitable valve for this purpose is available from the Burron OEM Division of B. Braun Medical, Inc. (Model No. 55401022).

Figure 3:
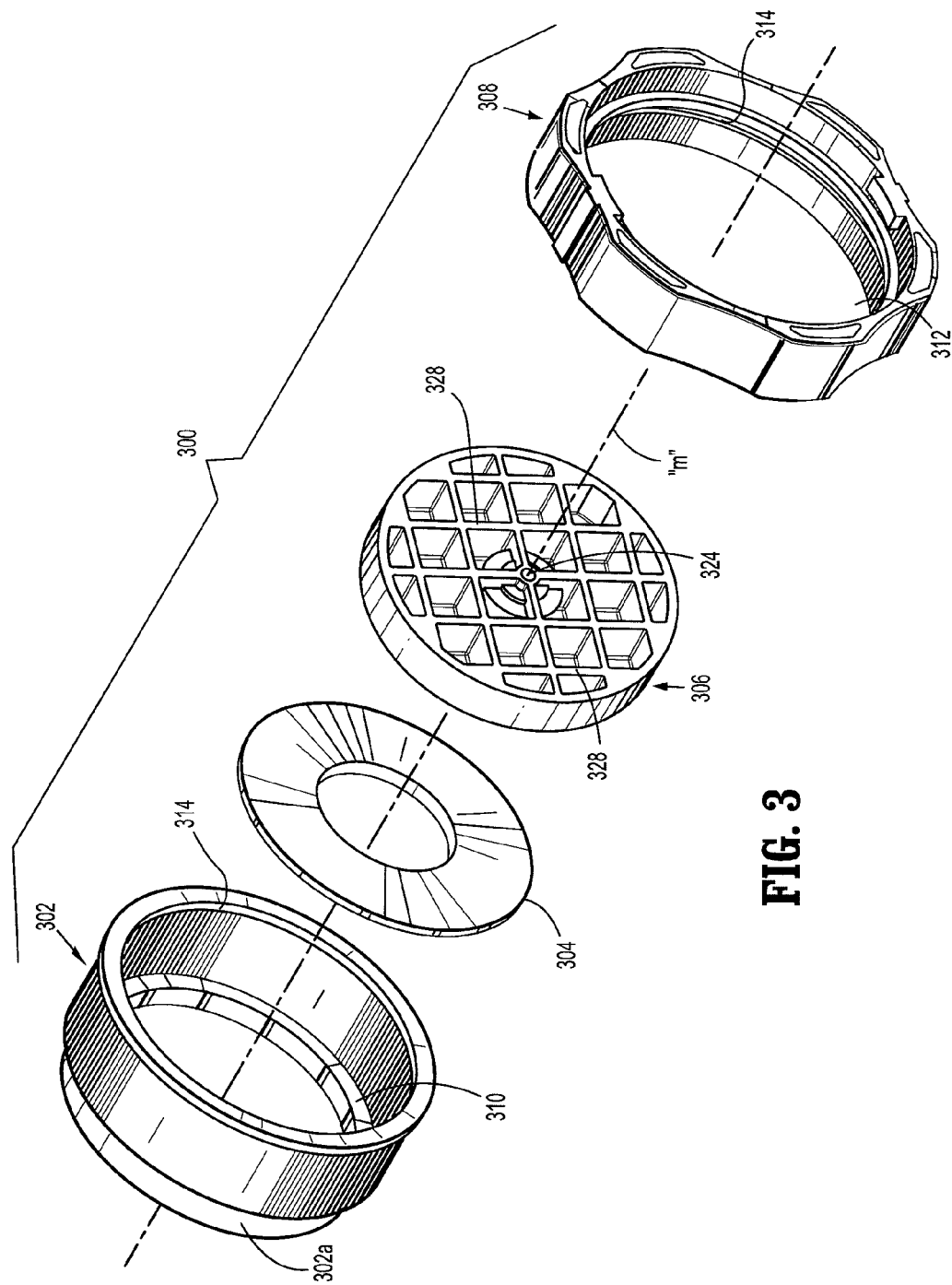
FIG. 3 is a perspective view with parts separated of the seal assembly of the surgical portal apparatus.
Figure 5:
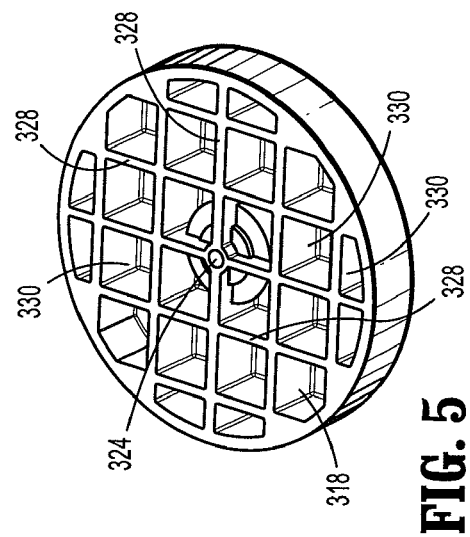
FIGS. 4 and 5 are frontal and rear perspective views of the seal member of the seal assembly.
Figure 7:
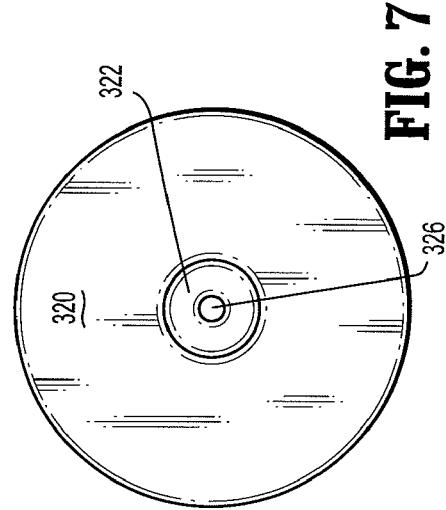
FIGS. 6 and 7 are front and rear plan views of the seal member of the seal assembly.
Figure 8:
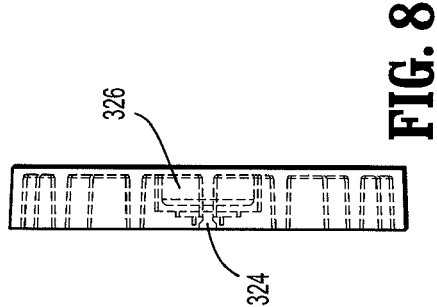
FIG. 8 is a side plan view of the seal member.
Figure 4:
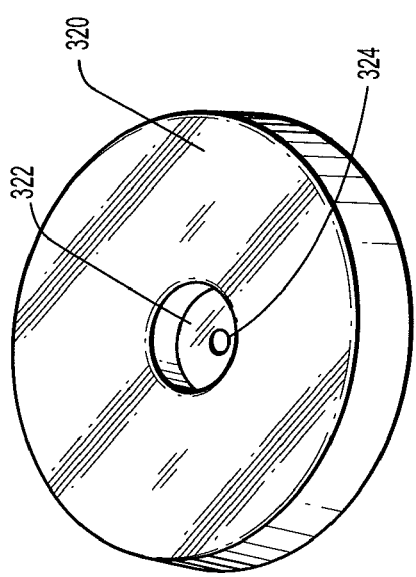
Figure 6:
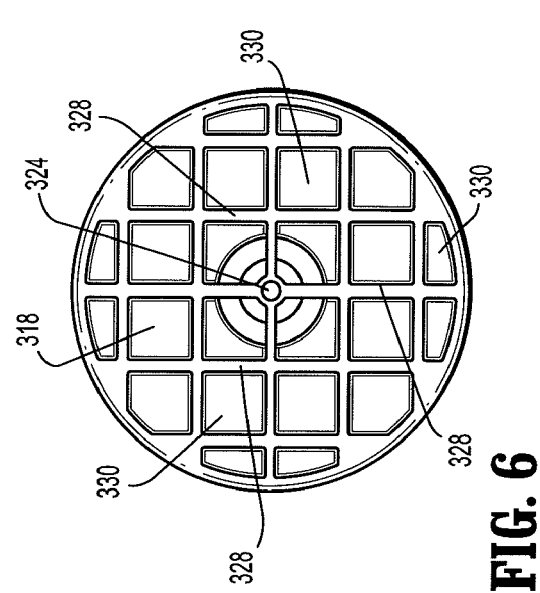

Referring now to FIG. 3, in conjunction with FIG. 2, the seal assembly 300 of surgical portal apparatus 100 will be described in detail. Seal assembly 300 includes end cap 302, stabilizer plate 304, seal member 306 and seal housing 308. End cap 302, stabilizer plate 304 and seal housing 308 form the outer seal body of seal assembly 300, which houses the sealing component, i.e., seal member 306.

End cap 302 is generally cylindrically-shaped and includes a proximal end portion 302a defining a diameter which is less than the diameter of the remaining portion of the end cap 302 and an inner peripheral ledge 310 which supports stabilizer plate 304. Stabilizer plate 304 defines an aperture 312 and assists in supporting seal member 306 and retaining the seal member 306 between end cap 302 and seal housing 308. Seal housing 308 includes central opening 312, and defines inner annular rib 314. Seal housing 308 receives end cap 302 when in the assembled condition to enclose the sealing components. The distal end face of seal housing 308 includes two opposed rib portions 316 extending radially inwardly. Rib portions 316 assist in mounting seal assembly 300 to portal assembly 200 as will be appreciated from the description provided below.

Referring now to FIGS. 4-8, in conjunction with FIGS. 2-3, seal member 306 will be discussed in detail. Seal member 306 is mounted within seal housing 308 by any conventional means. For example, seal member 306 may be secured within end cap 302 and secured between inner peripheral ledge 310 and inner annular rib 314 of seal housing 308. Seal member 306 may be secured within seal housing 308 in a manner to prevent longitudinal or radial movement of the entire seal member, i.e., secured in fixed relation with end cap 302 and seal housing 308.

Seal member 306 is generally disk shaped and defines leading (distal) and trailing (proximal) ends faces 318, 320. Trailing end face 320 includes an annular recess 322 generally concentrically arranged about seal axis "m". Annular recess 322 is in communication with central seal aperture or passage 324. Annular recess 322 may be adapted to receive and/or guide the surgical object toward seal aperture 324 during introduction of the surgical object.

Seal aperture 324 extends through leading and trailing end faces 318, 320 of seal member 300. Seal aperture 324 is defined within inner seal portions 326 (FIG. 2) and is adapted to expand upon insertion of the object whereby the inner seal portions 326 defining the seal aperture 324 establish a fluid tight seal about the surgical object. Although shown as a circular in configuration, seal aperture 324 may assume the configuration including rectangular and may also be in the form of a slit.

Leading end face 318 defines a grid or waffle structure having a plurality of interconnected struts 328 with recesses 330 therebetween. Struts 328 preferably extend in perpendicular arrangement to define rectangular or square recesses 330 at least adjacent central seal aperture 324. Recesses 330 adjacent the outer periphery of seal member 306 may include an arcuate outer side as provided by the circular periphery of the seal member.

Struts 328 define a lattice structure which is capable of flexing during offset or angular manipulation of a surgical object and return to its original configuration upon removal of the object. Moreover, the lattice or waffle geometry assists in preventing "cat-eyeing" that is caused by off-axis manipulation of the surgical object. In particular, struts 328 with the assistance of recesses 330 are capable of flexing to permit seal aperture 326 to follow the off-set motion of the instrument.

Seal member 306 may accommodate instruments ranging from 4.5 mm to about 12.5 mm in diameter, to seal against a minimum pressure of 12 mm Hg provided by an insufflated body cavity and create very little frictional force with instruments inserted through the seal member. Seal member 306 may be fabricated from suitable thermoplastic elastomers. In the alternative, seal member 306 may be fabricated from a low durometer thermoplastic elastomer or a gel material. Other materials are also envisioned.

The assembly of seal assembly 300 now will be discussed. Stabilizer plate 304 is positioned within end cap 302 such that the plate 304 rests on inner peripheral ledge 310 defined within the end cap 302. Thereafter, seal member 306 is positioned onto stabilizer plate 304. Seal housing 308 is positioned over the entire unit with the seal housing 308 receiving the distal portion of end cap 302. In this assembled condition, seal member 306 is trapped between inner peripheral ledge 310 of end cap 302 and annular rib 314 of seal housing 308.

Seal assembly 300 now in its fully assembled condition can be mounted to portal assembly 200. With reference to FIGS. 1-3, assembled seal assembly 200 is detachably mounted adjacent stabilizing plate 228 with the partial annular thread 228 (FIG. 2) of the stabilizing plate 220 being received within peripheral groove 322 defined in seal housing 308. Seal assembly 300 is rotated to cause engagement of the radially inwardly projecting rib portions 316 with partial annular thread 228 to releasably lock the seal assembly 200 to the cannula housing 202. Other means for detachably connecting the seal assembly 200 to cannula housing 202 can be readily determined by one skilled in the art such as screw threads, adhesives, bayonet locking, and the like.

Figure 10:
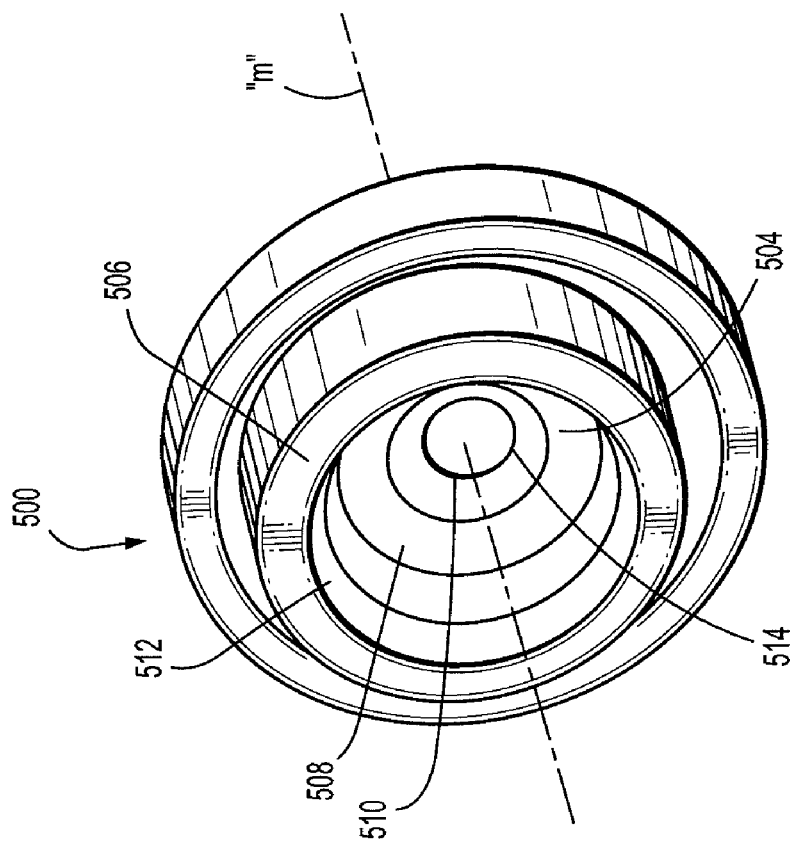
FIGS. 9 and 10 are frontal and rear perspective views of an alternate embodiment of the seal member of the seal assembly.
Figure 9:
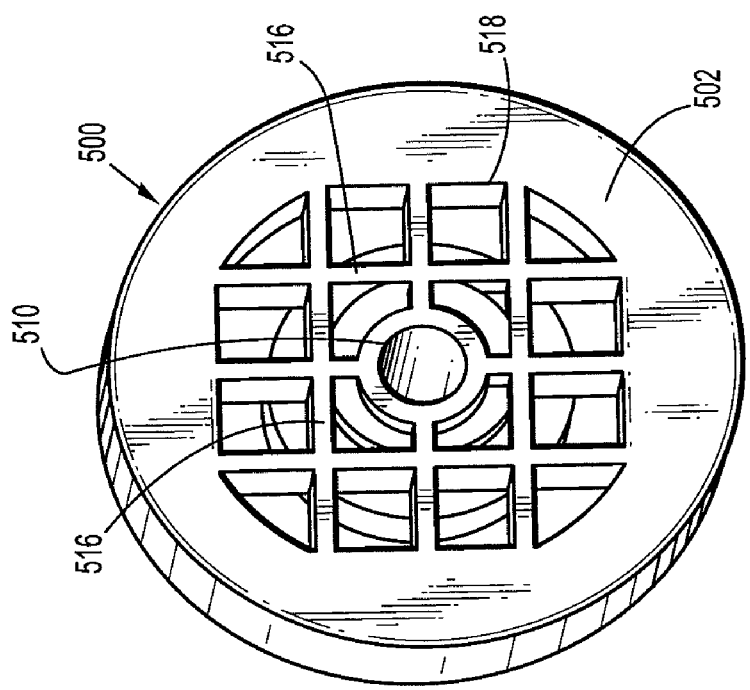

FIGS. 9-10 illustrate an alternate embodiment of seal member 500. In accordance with this embodiment, seal member 500 includes leading and trailing end faces 502, 504. Trailing or proximal end face 504 includes an annular wall 506 depending therefrom. Annular wall 506 defines an enlarged aperture 508 for receiving the surgical object to guide the surgical object toward seal aperture 510. Annular wall 506 may include inner tapered wall surface 512 to also assist in guiding the surgical object toward the seal axis "m". Trailing end face 504 further defines a tapered wall surface 514 circumscribing seal aperture 510 to guide the surgical object toward the aperture.

Leading end face 502 of seal member 500 includes a gridiron or waffle arrangement defined by a plurality of perpendicular struts 516 in intersecting relation. Adjacent parallel struts 516 are spaced a greater distance than the prior embodiment to define relatively enlarged rectangular recesses 518. This arrangement may provide greater flexibility than the embodiment of FIGS. 1-8 to further assist or permit offset manipulation of the surgical object.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. A surgical portal apparatus, which comprises:
   a portal housing;
   an elongated portal member connected to the portal housing and depending therefrom, the portal member defining a central longitudinal axis, the portal housing and the portal member having an axial bore for reception and passage of a surgical object; and
   a seal member comprising a resilient material and being mounted to the portal housing, the seal member including leading and trailing end faces and having inner portions defining a passage to permit passage of the surgical object, one of the leading and trailing end faces having a plurality of recessed cells formed within intersecting struts to define a general waffle-like pattern or profile, at least some of the recessed cells define a generally rectangular arrangement, the at least some of the recessed cells axially arranged in a row, the intersecting struts being relatively flexible to flex upon radial offset manipulation of the object to permit corresponding movement of the passage while substantially maintaining a seal about the surgical object.

2. The surgical portal apparatus according to claim 1 wherein the leading end face of the seal member has the recessed cells.

3. The surgical portal apparatus according to claim 2 wherein the trailing end face of the seal member defines a seal recess circumscribing the passage to facilitate reception and passage of the surgical object through the passage.

4. The surgical portal apparatus according to claim 3 wherein the seal recess is generally annular.

5. The surgical portal apparatus according to claim 2 wherein the seal member includes an annular seal collar depending from the trailing end face.

6. A surgical portal apparatus, which comprises:
   a portal housing;
   an elongated portal member connected to the portal housing and depending therefrom, the portal member defining a central longitudinal axis, the portal housing and the portal member having an axial bore for reception and passage of a surgical object; and
   a seal member comprising a resilient material and being mounted to the portal housing, the seal member including leading and trailing end faces and having inner portions defining a passage to permit passage of the surgical object, the leading end face defining a plurality of recessed cells formed within intersecting struts, at least some of the recessed cells being arranged in a linear manner with respect to each other, the intersecting struts being relatively flexible to flex upon radial offset manipulation of the object to permit corresponding movement of the passage while substantially maintaining a seal about the surgical object, the seal member includes an annular seal collar depending from the trailing end face, the trailing end face having an internal tapered wall circumscribing the passage to facilitate alignment of the surgical object with the passage during passage through the seal member.

7. The surgical portal apparatus according to claim 6 wherein the annular seal collar includes an internal wall surface, the wall surface being tapered to facilitate alignment of the surgical object with the passage during introduction of the surgical object within the seal member.

8. The surgical portal apparatus according to claim 1 wherein the seal member defines an aperture therethrough, the aperture being the passage.

9. The surgical portal apparatus according to claim 1 wherein the seal member comprises a gel material.

10. The surgical portal apparatus according to claim 1 including a zero closure seal adapted to substantially close the axial bore in the absence of the surgical object.

11. The surgical portal apparatus according to claim 6 wherein the internal tapered wall circumscribing the passage is disposed radial inward of the annular seal collar.

12. The surgical portal apparatus according to claim 11 wherein the internal tapered wall is substantially planar.

13. The surgical portal apparatus according to claim 6 wherein the recessed cells and the interconnected struts define a general waffle-like pattern or profile.

14. The surgical portal apparatus according to claim 6 wherein at least some of the recessed cells define a generally rectangular arrangement.

15. A surgical portal apparatus, which comprises:
   a portal housing;
   an elongated portal member connected to the portal housing and depending therefrom, the portal member defining a central longitudinal axis, the portal housing and the portal member having an axial bore for reception and passage of a surgical object; and
   a seal member comprising a resilient material and being mounted to the portal housing, the seal member including leading and trailing end faces and having inner portions defining a passage to permit passage of the surgical object, the leading end face defining a plurality of recessed cells formed within intersecting struts, adjacent recessed cells being defined at least in part by a common intersecting strut therebetween, the interconnected struts being relatively flexible to flex upon radial offset manipulation of the object to permit corresponding movement of the passage while substantially maintaining a seal about the surgical object, the trailing end face having a substantially planar internal tapered wall circumscribing and coterminous with the passage to facilitate alignment of the surgical object with the passage during passage through the seal member.

16. The surgical portal apparatus according to claim 15 wherein the recessed cells and the intersecting struts define a general waffle-like pattern or profile.

* * * * *